United States Patent [19]

Pruitt et al.

[11] Patent Number: 5,993,399
[45] Date of Patent: *Nov. 30, 1999

[54] AUTOMATED TISSUE SAMPLING DEVICE

[75] Inventors: Terrell A. Pruitt, Lawrenceville; David C. Field, Snellville; Charles N. Jacobs, Conyers, all of Ga.

[73] Assignee: C.R. Bard, Inc., Murray Hill, N.J.

[ * ] Notice: This patent is subject to a terminal disclaimer.

[21] Appl. No.: 09/203,071

[22] Filed: Dec. 1, 1998

Related U.S. Application Data

[63] Continuation of application No. 08/691,810, Jul. 31, 1996, Pat. No. 5,842,999.

[51] Int. Cl.[6] .................................................. A61B 10/00
[52] U.S. Cl. ........................... 600/562; 600/566; 600/567
[58] Field of Search ..................... 600/562, 566, 600/567; 606/167, 170

[56] References Cited

U.S. PATENT DOCUMENTS

| | | | |
|---|---|---|---|
| 3,477,423 | 11/1969 | Griffith | 128/751 |
| 4,699,154 | 10/1987 | Lindgren | 128/754 |
| 4,924,878 | 5/1990 | Nottke | 128/751 |
| 4,944,308 | 7/1990 | Akerfeldt | 128/751 |
| 4,958,625 | 9/1990 | Bates et al. | 128/754 |
| 5,036,860 | 8/1991 | Leigh et al. | 128/754 |
| 5,172,702 | 12/1992 | Leigh et al. | 128/754 |
| 5,284,156 | 2/1994 | Schramm et al. | 128/754 |
| 5,368,045 | 11/1994 | Clement et al. | 128/754 |

*Primary Examiner*—Max Hindenburg
*Attorney, Agent, or Firm*—Jones & Askew, LLP

[57] ABSTRACT

An automated tissue sampling device is disclosed which permits its needles to be cocked either simultaneously or sequentially and can be cocked with only one hand. The cocking mechanism is arranged so as to virtually eliminate the possibility that the needles will be cocked in the wrong sequence. The physician can readily confirm, either visually or tactilely, whether the device is uncocked, half cocked, or fully cocked. The disclosed tissue sampling device also comprises two different trigger buttons, one adjacent the front end of the device and the other at the rear, and manipulating either of the two trigger buttons will actuate the device.

7 Claims, 7 Drawing Sheets

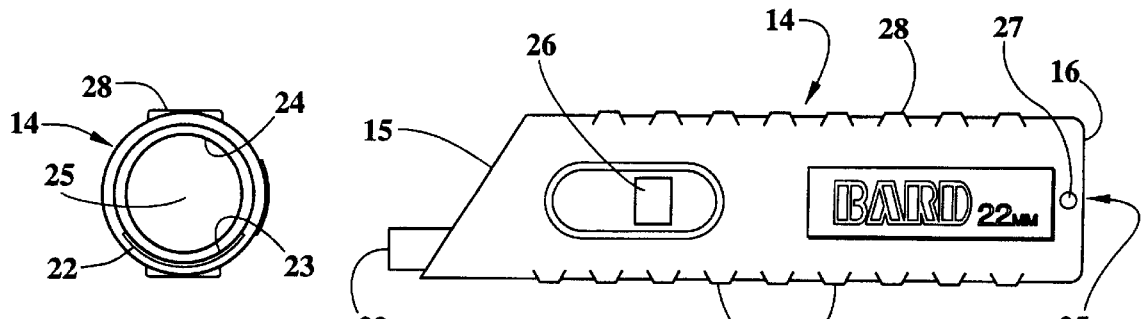
*Fig. 2C*  *Fig. 2A*
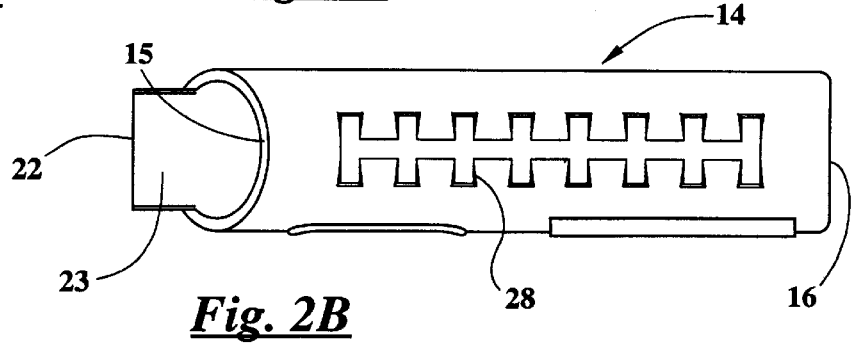
*Fig. 2B*
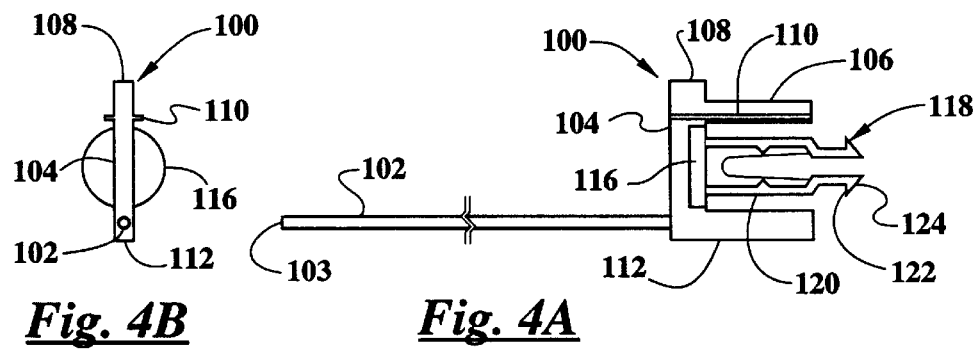
*Fig. 4B*  *Fig. 4A*
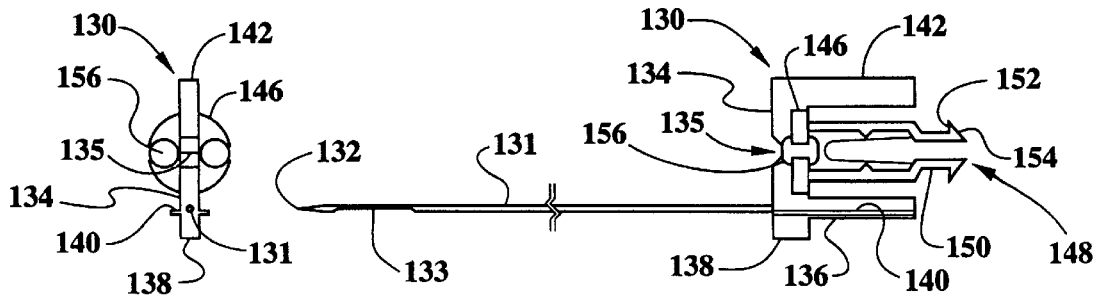
*Fig. 5B*  *Fig. 5A*

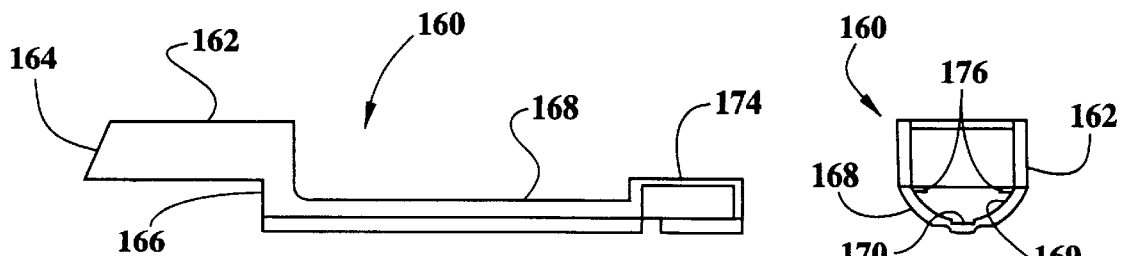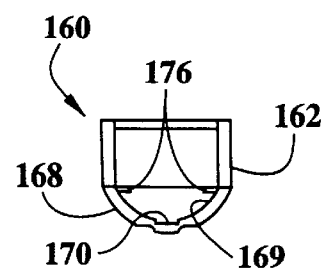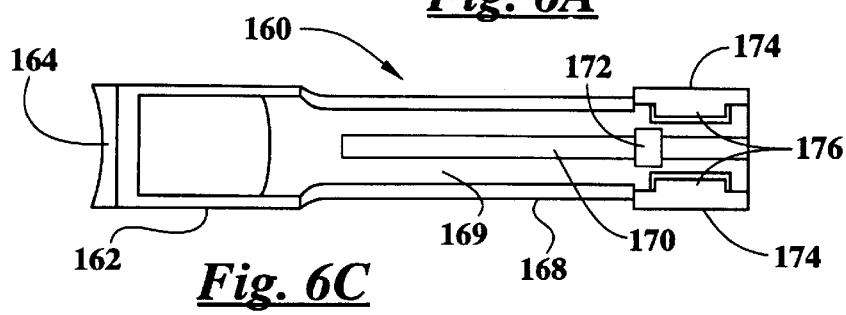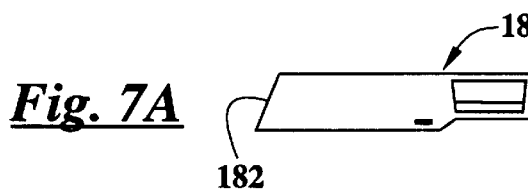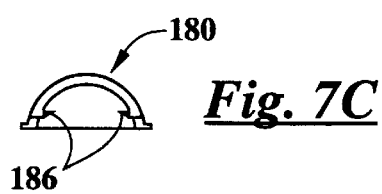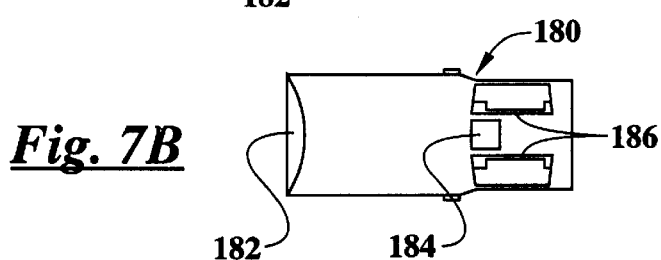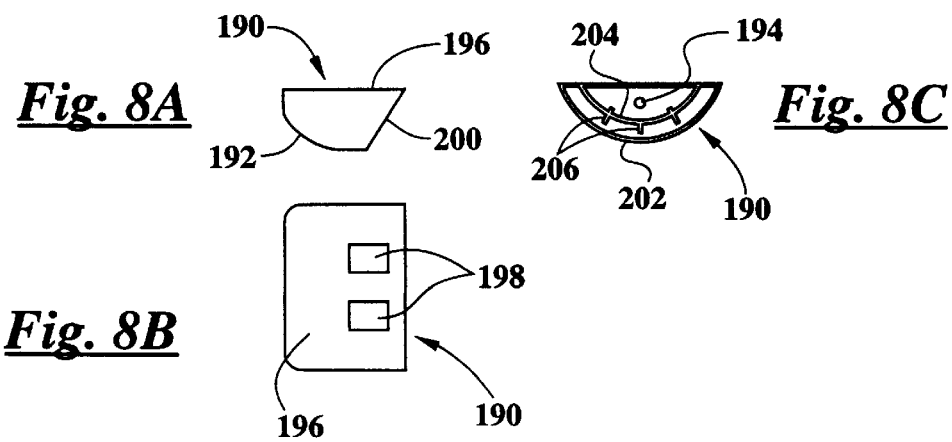

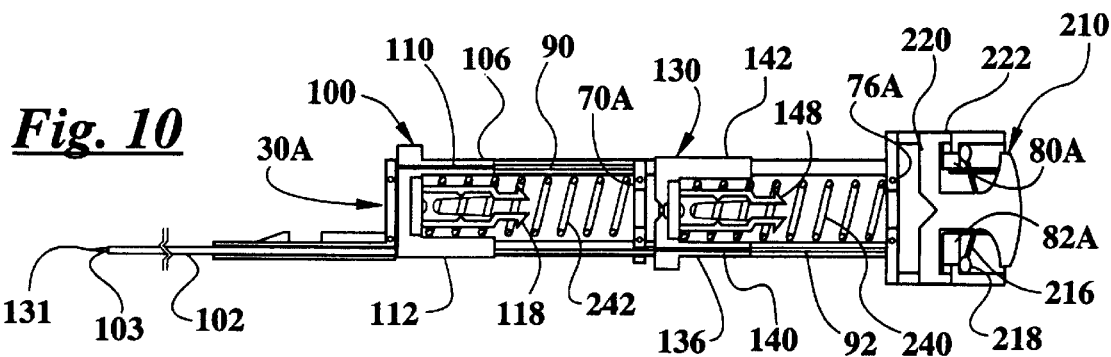
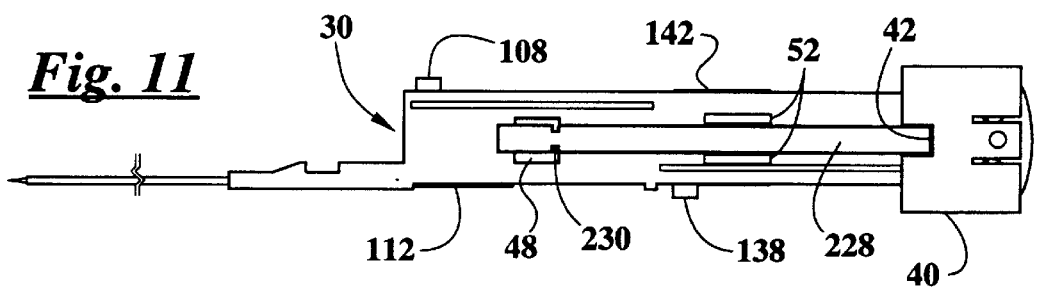
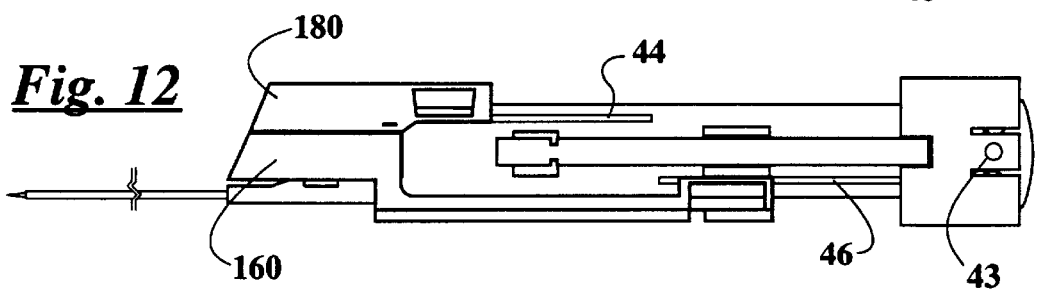
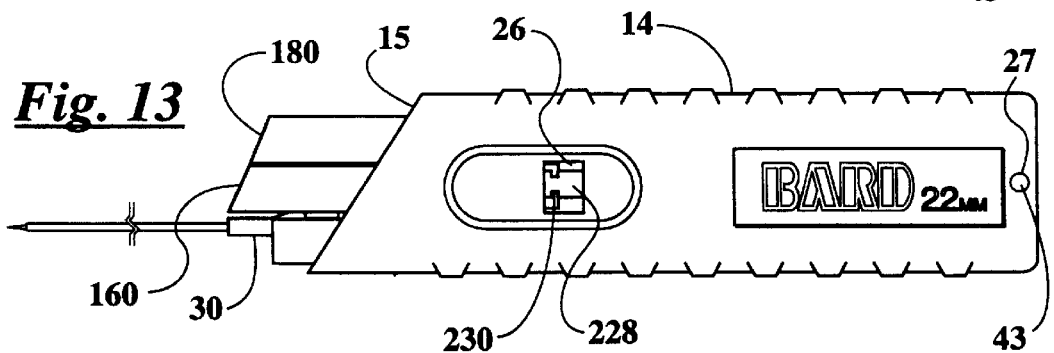
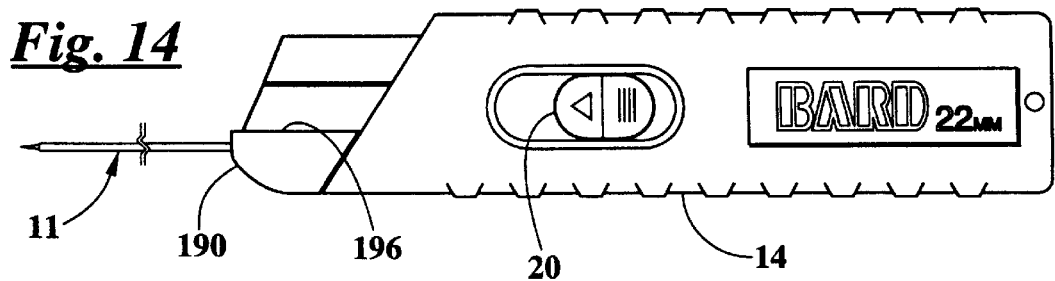

020
AUTOMATED TISSUE SAMPLING DEVICE

This application is a continuation application of Ser. No. 08/691,810 filed Jul. 31, 1996 now U.S. Pat. No. 5,842,999.

TECHNICAL FIELD

The present invention relates generally to automated tissue sampling devices for retrieving tissue specimens from patients for biopsy purposes. More specifically, the invention relates to an automated tissue sampling device which provides the advantage of being able to cock both needles of the device simultaneously with a single action, while still permitting a tissue specimen to be recovered from the tissue receiving recess of the stylet without having to dismount the needle from the driving unit.

BACKGROUND OF THE INVENTION

Since the late 1960's, the preferred biopsy needle configuration for retrieving core tissue samples for biopsy purposes has been the so-called "Tru-Cut"-type needle assembly. This biopsy needle assembly, which is the subject of U.S. Pat. No. 3,477,423 to Griffith et al., comprises two elements, a hollow tubular cannula and a solid stylet slidably disposed within the cannula. The stylet has a sharpened forward end and a tissue receiving recess located just rearward of the forward end. The cannula has a sharpened forward edge. To retrieve a tissue specimen using the "Tru-Cut"-type biopsy needle assembly, the stylet and cannula are introduced into the patient and advanced to a point just short of the target tissue. The stylet is then manually advanced into the target tissue, and tissue prolapses into the tissue receiving recess adjacent to the forward end of the stylet. The cannula is then manually advanced, shearing off the tissue within the tissue receiving recess of the stylet and capturing the specimen. The stylet and cannula are then withdrawn together, and the tissue sample removed for analysis.

Despite its numerous advantages over then prior art biopsy needles, the "Tru-Cut"-type needle was somewhat difficult to use. Since manual advancement of the stylet occurred relatively slowly, the target tissue was sometimes pushed aside, rather than prolapsing into the tissue-receiving recess of the stylet, such that the resulting tissue specimen was not of the target tissue. Further, in the course of the physician's manually advancing the cannula, there was a tendency for the stylet to be withdrawn from the target tissue, resulting in a poor tissue specimen or even no specimen at all. These problems were addressed beginning in the early 1980's with automated, spring-actuated driving units which would be coupled to a "Tru-Cut"-type needle assembly. When the driving unit was fired, the stylet would be released, and a spring would drive the stylet forward a predetermined distance. When the stylet reached the forward extent of its travel, the cannula would instantly be released, and a spring associated with the cannula would drive it forward over the stylet, shearing off the tissue specimen and capturing it within the forward end of the cannula. This device is disclosed in PCT Application Serial No. SE83/00112.

This device, though a great improvement over a manually operated "Tru-Cut" needle, was somewhat inconvenient to operate in that a separate cocking tool had to be used to pry back slides within the driving unit to which the respective needles were coupled. This inconvenience was addressed by a device disclosed in U.S. Pat. No. 4,699,154 to Lindgren et al., which included an integral cocking slide. Actuation of the slide would simultaneously draw both needles to their cocked positions.

While both of the automated devices disclosed in PCT Application Serial No. SE83/00112 and U.S. Pat. No. 4,699,154 represented significant advances over the manually operated "Tru-Cut" needle, they were nonetheless inconvenient in certain respects. In the case of both instruments it was necessary to remove the needle assembly from the driving unit before the tissue specimen could be retrieved from the tissue receiving notch at the far end of the stylet. This problem was addressed by a device disclosed in U.S. Pat. No. 4,944,308, which had a cocking mechanism which retracted the needles sequentially, rather than simultaneously. In this manner, the cannula could be retracted without retracting the stylet, thereby affording access to the tissue receiving recess and the stylet. The cocking mechanism in the aforesaid U.S. Pat. No. 4,944,308 comprised a rotatable sleeve on the outside of the housing. Rotating the sleeve a first time cocked the cannula, and rotating the sleeve a second time cocked the stylet.

Another device which permitted independent cocking of the cannula and stylet was disclosed in U.S. Pat. No. 4,958,625, wherein the needles were cocked by slides mounted to the housing. Operating the cannula slide without operating the stylet slide would retract the cannula with respect to the stylet, thereby exposing the tissue receiving notch.

While addressing some of the inconveniences of earlier automated biopsy devices, the devices disclosed in U.S. Pat. Nos. 4,944,308 and 4,958,625 had their own disadvantages. Cocking the respective needles independently required two separate actions on the part of the physician, one for each needle. In addition, the device disclosed in U.S. Pat. No. 4,944,308 required two hands to cock the device, one hand to grasp the instrument and the other hand to rotate the sleeve. Further, the device disclosed in U.S. Pat. No. 4,958,625 comprised two slides, and it was not intuitive to the physician which slide should be cocked first. Thus the possibility existed that, in an effort to recover the tissue specimen from the tissue receiving notch, the stylet slide would be cocked first, such that the tissue sample was not exposed.

Thus, there is a need for an automated biopsy device which provides for the cannula to be cocked independently of the stylet to permit a tissue specimen to be recovered from the tissue receiving recess of the stylet, wherein the cocking order is intuitive to the physician so as to minimize the possibility that the needles are cocked in the wrong sequence.

There is a further need for an automated biopsy device which provides the advantage of being able to cock both needles simultaneously with a single action, while still permitting a tissue specimen to be recovered from the tissue receiving recess of the stylet without having to dismount the needle from the driving unit.

There is a further need for an automated biopsy device which provides the advantage of being able to cock both needles simultaneously with a single action and which permits one-handed cocking.

Another inconvenience associated with prior art automated biopsy devices concerns the location of the trigger element by which the instrument is fired. All of the aforementioned devices except one had the trigger located on the rear of the housing, a location well-suited for procedures in which the instrument would be held substantially upright. However, depending upon the style of the individual physician and the nature of the procedure being performed, there are instances in which a trigger on the side of the housing, as disclosed in U.S. Pat. No. 4,958,625, is more convenient. Neither trigger location, however, is optimal for all procedures and for all physicians.

Thus there is a need for an automated biopsy device which permits the device to be actuated from either the front or the back of the housing, depending upon the style of the individual physician and the procedure being performed.

SUMMARY OF THE INVENTION

Stated generally, the present invention comprises an automated biopsy device which, in a first aspect, provides the advantage that the sequence in which the needles are cocked is intuitive to the physician, thereby minimizing the possibility that the needles will be cocked in the wrong order. In another aspect, the automated biopsy device of the present invention provides the advantage of being able to cock both needles simultaneously with a single action, while still permitting a tissue specimen to be recovered from the tissue receiving recess of the stylet without having to dismount the needle from the driving unit. According to a further aspect of the present invention, the device can be actuated from either of two locations on the housing, depending upon the style of the individual physician and the procedure being performed. And in yet another aspect of the present invention, a bumper means is operatively associated with the second needle hub for engaging a stop to limit the forward extent of movement of the second needle hub. The bumper means is comprised of a resilient, deformable material such that it deforms upon engaging the stop to permit the second needle hub to reach the forward extent of its movement and release the second latch means. The bumper then returns to its normal configuration such that the second needle hub is displaced rearward from the forward extent of its movement and away from the second latch means.

Stated somewhat more specifically, the present invention relates to a tissue sampling device comprising a housing having first and second needle hubs mounted therewithin for movement along the longitudinal axis of the housing;. A hollow first needle has one end coupled to the first needle hub, the hollow first needle extending along the longitudinal axis of the housing through an opening in the front housing end. A second needle is slidably disposed within the hollow first needle, one end of the second needle being coupled to the second needle hub. The second needle has a tip at one end and a tissue sample receiving recess adjacent the tip. A first spring is operatively associated with the second needle hub and is capable of being placed in an energized mode to store energy, the first spring being releasable from its energized mode to propel the second needle hub forward such that the tissue sample receiving recess of the second needle is extended from the hollow first needle, whereby a tissue sample can be captured within the recess. A second spring is operatively associated with the first needle hub and is also capable of being placed in an energized mode to store energy, the second spring being releasable from its energized mode to propel the first needle hub forward such that the tissue sample receiving recess of the second needle is enclosed by the hollow first needle. A first latch means selectively releasable from outside the housing releasably holds the second spring in its energized mode, and a second latch means releasably holds the first spring in its energized mode, the second latch means being releasable in response to and subsequent to release of the first latch means.

In a first aspect, the present invention comprises first and second slides movably mounted to the housing and coupled to the first and second needle hubs respectively. The slides each have a finger receiving portion, whereby the needle hubs can be retracted by exerting a rearward force against the finger receiving portions of the slides to place the springs in their energized modes. The first and second slides are arranged relative to one another such that the finger receiving portions of the first and second slides can be contacted simultaneously by a single finger of an operator. In the disclosed embodiment the finger receiving portions of the slides are located adjacent the forward end of the housing, the second slide is located on top of the first slide, and the finger receiving portions of the slides lie in a common plane.

In a second aspect, the present invention comprises first and second trigger means mounted to the housing, both the first and second trigger means being linked to the first latch means such that actuation of either of the first and second triggers is operative to release the first latch means. In the disclosed embodiment one of the trigger means is mounted to the housing adjacent its front end and the other trigger means is located at the rear end of the housing.

In yet another aspect of the invention, a bumper means is operatively associated with the second needle hub for engaging a stop formed on the housing to limit the forward extent of movement of the second needle hub. The bumper means is comprised of a resilient, deformable material such that it deforms upon engaging the stop to permit the second needle hub to reach the forward extent of its movement and release the second latch means. The bumper then returns to its normal configuration such that the second needle hub is displaced rearward from the forward extent of its movement and away from the second latch means.

Thus it is an object of the present invention to provide an improved automated tissue sampling device.

It is another object of the present invention to provide an improved automated tissue sampling device in which both needles can be cocked simultaneously with a single action, while still permitting a tissue specimen to be recovered from the tissue receiving recess of the stylet without having to dismount the needle from the driving unit.

Still another object of the present invention is to provide an automated biopsy device which affords the advantage of being able to cock both needles simultaneously with a single action and which permits one-handed cocking.

It is yet another object of the present invention to provide an automated biopsy device which permits the device to be actuated from either the front or the back of the housing, depending upon the style of the individual physician and the procedure being performed.

Other objects, features, and advantages of the present invention will become apparent upon reading the following specification, when taken in conjunction with the drawings and the appended claims.

BRIEF DESCRIPTION OF THE DRAWINGS

FIG. 2A is a side view of an outer housing of the biopsy instrument of FIG. 1; FIG. 2B is a top view of the outer housing of FIG. 2A; and FIG. 2C is a front view of the outer housing of FIG. 2A.

FIG. 4A is a side view of a cannula and cannula hub of the biopsy instrument of FIG. 1; FIG. 4B is a front view of the cannula and cannula hub of FIG. 4A.

FIG. 5A is a side view of a stylet and stylet hub of the biopsy instrument of FIG. 1; FIG. 5B is a front view of the stylet and stylet hub of FIG. 5A.

FIG. 6A is a side view of a stylet cocking slide of the biopsy instrument of FIG. 1; FIG. 6B is a top view of the stylet cocking slide of FIG. 6A; and FIG. 6C is a rear view of the stylet cocking slide of FIG. 6A.

FIG. 7A is a side view of a cannula cocking slide of the biopsy instrument of FIG. 1; FIG. 7B is a top view of the cannula cocking slide of FIG. 7A; and FIG. 7C is a rear view of the cannula cocking slide of FIG. 7A.

FIG. 8A is a side view of a retainer of the biopsy instrument of FIG. 1; FIG. 8B is a top view of the retainer of FIG. 8A; and FIG. 8C is a rear view of the retainer of FIG. 8A.

FIGS. 10–14 illustrate the assembly sequence of the biopsy instrument of FIG. 1, where FIG. 10 is a side view showing the cannula and cannula hub, stylet and stylet hub, and trigger assembly mounted within the inner housing half of FIG. 3D; FIG. 11 is a side view of the inner housing of FIGS. 3A–3D showing the trigger assembly, stylet, and cannula mounted thereto; FIG. 12 is a side view of the assembly of FIG. 11 showing the stylet and cannula cocking slides mounted thereto; FIG. 13 is a side view showing the assembly of FIG. 12 inserted into the outer housing; and FIG. 14 is a side view showing the assembly of FIG. 13 with a retainer and trigger slide mounted thereto.

FIG. 17 is a schematic diagram depicting the cannula and cannula hub, the stylet and stylet hub, and the trigger assembly, with the stylet and cannula in their cocked positions; FIG. 18 shows the assembly of FIG. 17 with the trigger assembly actuated to release the stylet; FIG. 19 shows the assembly of FIG. 17 with the stylet advanced to its forward most position and the stylet hub releasing the cannula from its locked position; and FIG. 20 shows the assembly of FIG. 17 with the cannula advanced to its forwardmost position.

DETAILED DESCRIPTION OF THE DISCLOSED EMBODIMENT

Figure 1:
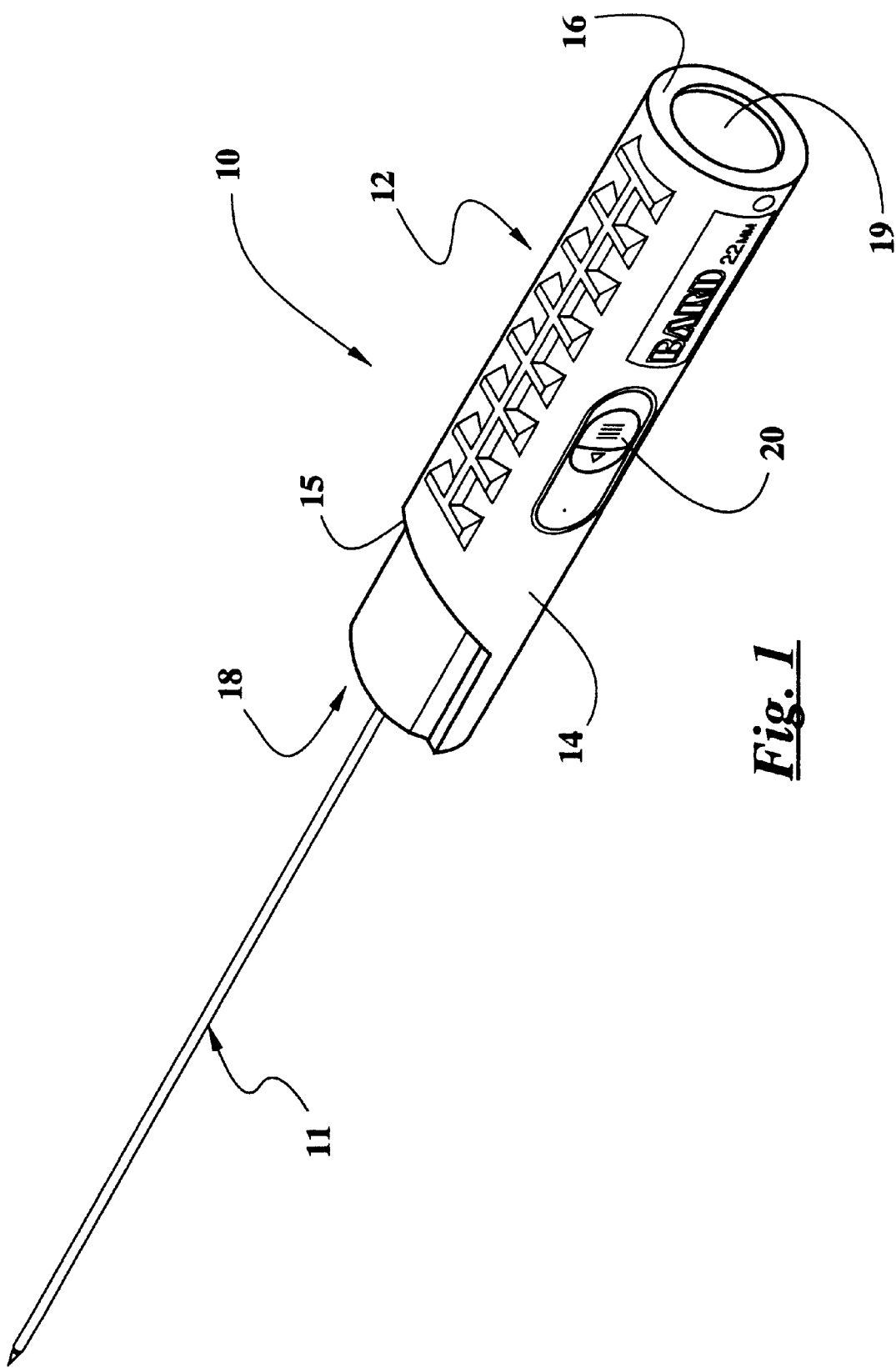
FIG. 1 is a perspective view of an automated biopsy instrument according to the present invention.

Referring now to the drawings, in which like numerals indicate like elements throughout the several views, FIG. 1 illustrates a biopsy instrument 10 according to the present invention. The biopsy instrument 10 includes a needle assembly 11 and a driving unit 12. The driving unit 12 comprises a generally cylindrical outer housing 14 having a front end 15 and a back end 16. The needle assembly 11 projects forward from the front end 15 of the outer housing 14. A cocking mechanism 18 is seen at the front end of the outer housing 14. A rear-mounted trigger button 19 is mounted at the back end 16 of the outer housing 14, and a side-mounted trigger button 20 is mounted on the side of the outer housing 14.

Referring now to FIGS. 2A–2C, the outer housing 14 generally takes the shape of a hollow cylinder having an angled front end 15. A curved tongue 22 is formed at the lower edge of the front end 15 of the outer housing 14. The upper surface 23 of the tongue 22 conforms to the curvature of the inner diameter of the cylindrical wall of the outer housing 14. At the back end 16 of the outer housing 14, an annular wall 24 extends inward and defines a circular opening 25. A rectangular opening 26 is formed in the side of the outer housing 14 adjacent its front end 15. A circular locating hole 27 is formed in the side wall of the outer housing 14 adjacent its back end 16.

A plurality of raised ridges 28 are formed on the upper and lower surfaces of the outer housing 14. The ridges 28 serve a number of purposes. First, the ridges 28 provide a gripping surface by which the physician can securely hold the instrument 10. Second, the ridges serve as locator surfaces by which the physician can discern the orientation of the instrument by feel. Third, the flat upper surfaces of the ridges 28 prevent the instrument 10 from rolling when set down on a flat surface. And finally, the pattern of the ridges 28 is distinctly decorative.

Figure 3A:
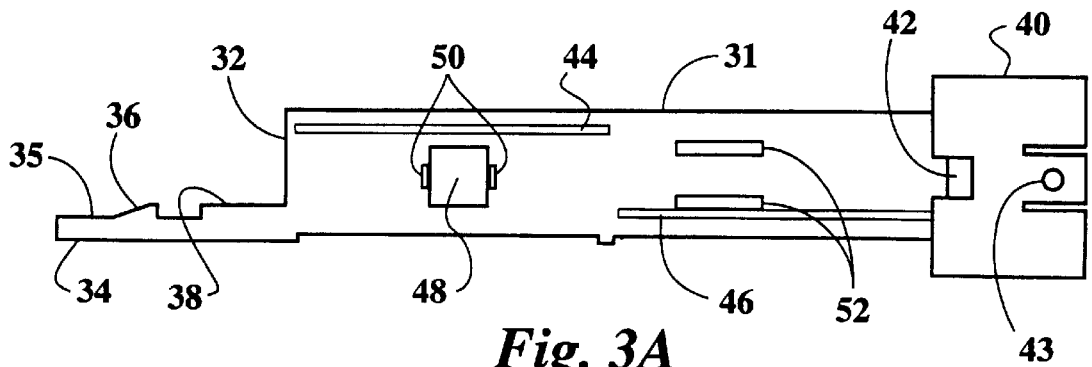
FIG. 3A is side view of an inner housing of the biopsy instrument of FIG. 1.
Figure 3B:
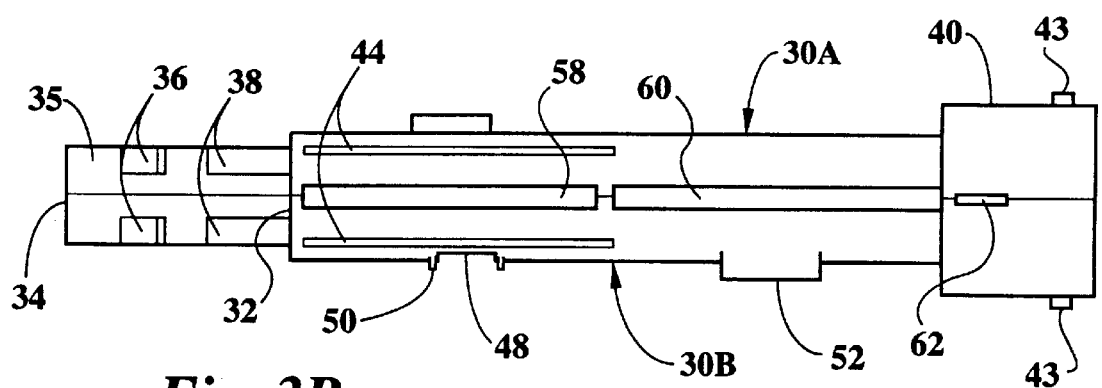
FIG. 3B is a top view of the inner housing of FIG. 3A.
Figure 3C:
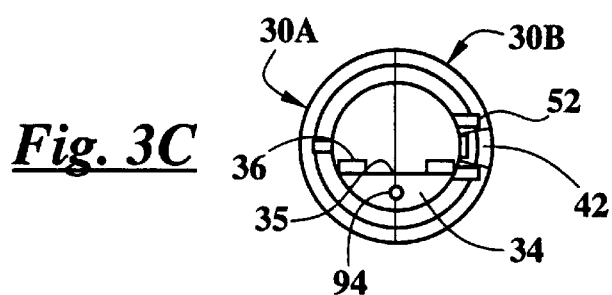
FIG. 3C is a front view of the inner housing of FIG. 3A.

FIGS. 3A–3C illustrate an inner housing 30 comprised of inner housing halves 30A, 30B. The main body 31 of the inner housing 30 is generally cylindrical and has a front end 32. A nose portion 34 projects forward from the front end 32 of the main body portion 31 of the inner housing 30. The lower surface of the nose portion 34 follows the cylindrical contour of the outer circumference of the main body portion 31 of the inner housing 30, while the upper surface 35 of the nose portion 34 is generally flat. A pair of angled upsets 36 are formed on the upper surface 35 of the nose portion 34 at an intermediate location thereon. A pair of raised stop members 38 are formed on the upper surface 35 of the nose portion 34 at the rearward portion thereof. As seen in FIG. 3C, a circular bore 39 is formed through the nose portion 34 of the inner housing 30 and extends parallel to the longitudinal axis of the inner housing.

The inner housing 30 further comprises an enlarged cylindrical rear portion 40 at the back end of the main body portion 31. A rectangular opening 42 is formed in the rear portion 40 in the left inner housing half 30B. Locating pins 43 project outward from the rear portion 40 of the inner housing 30.

Grooves 44 are formed in an upper portion of the inner housing 30, extending along both sides of the main body portion 31 of the inner housing 30 from a point adjacent the front end 32 of the main body portion 31 and extending to approximately the midpoint of the main body portion. Similar grooves 46 are formed on a lower portion of the main body portion 31 of the inner housing 30 extending from a midpoint of the main body portion rearward.

A rectangular opening 48 is formed in the left inner body half 30B at a location near the front end 32 of the main body portion 31. The location of the rectangular opening 48 is such that when the inner housing 30 is positioned within the outer housing 14 as will hereinafter be described, the rectangular opening 48 in the inner housing 30 is in register with the rectangular opening 26 in the outer housing 14. A pair of tabs 50 project upward along either side of the rectangular opening 48 in the left inner housing half 30B. A pair of elongate guide tabs 52 in spaced apart relation and extending generally parallel to the longitudinal axis of the inner housing 30 project outward from the left inner housing half 30B. A tab 54 projects outward from the right inner housing half 38. The height of the tabs 52, 54 is such that the inner housing 30 is positioned within the outer housing 14, the outer edges of the tabs bear against the inner walls of the outer housing 14 to stabilize the inner housing 30 within the outer housing.

Cannula hub guide channels 58 are formed in the upper and lower walls of the inner housing 30 extending from a location adjacent to the front end 32 of the main body portion 31 to a location adjacent the midpoint of the main body portion. Stylet hub guide channels 60 are formed in the upper and lower walls of the inner housing 30 extending from a location just rearward of the cannula hub guide channel 58 and extending to the rear end of the main body portion 31. Trigger assembly retention slots 62 are formed in the upper and lower walls of the enlarged cylindrical rear portion 40 of the inner housing 30.

Figure 3D:
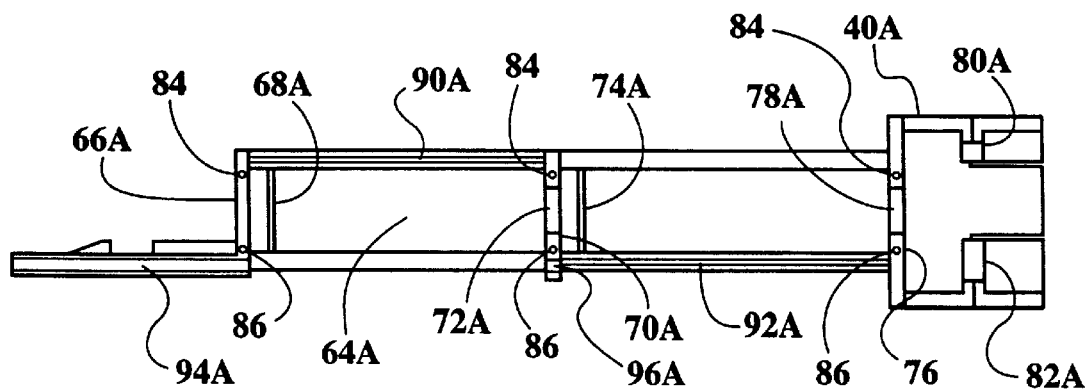
FIG. 3D is a side view of one of the inner housing halves which comprise the inner housing of FIG. 3A, showing interior detail.

FIG. 3D shows the interior of the right housing half 30A. Except as may be specifically pointed out, it will be understood that the opposite inner housing half 30B has the same internal configuration as the right inner housing half 30A. In addition, where elements are identified with the suffix "A," it will be understood that the particular element is associated with the right housing half 30A and that there is a corresponding element in the left housing half 30B. It will further be understood that where there is a component identified by a numeral and another component identified by that same numeral and the suffix "A" or "B," the component with the suffix forms a part of the component identified by the corresponding numeral without a suffix.

The inner housing half 30A comprises a semi-cylindrical cavity 64A. When the inner housing halves 30A, 30B are assembled, the semi-cylindrical cavity 64A in the right inner housing half 30A mates with a corresponding semi-cylindrical cavity in the left housing half 30B to form a generally cylindrical cavity. A front wall section 66A extends the full width of the semi-cylindrical cavity 64A of the right inner housing half 30A. When the housing halves 30A, 30B are assembled, the front wall section 66A mates with a corresponding front wall in the opposite housing half to form a closed front wall of the main body portion 31 of the inner housing 30. A stop member 68A is formed just rearward of the front wall section 66A. The stop member 68A has a width which is less than the depth of the semi-cylindrical cavity 64A such that when the housing halves 30A, 30B are assembled, there is a gap between the stop member 68A and a corresponding stop member in the opposite housing half.

The right housing half 30A further comprises an intermediate wall 70A having a semi-cylindrical opening 72A therethrough. When the inner housing halves 30A, 30B are assembled, the intermediate wall 70A mates with a corresponding intermediate wall in the opposite housing half to form a wall having a cylindrical bore therethrough. A stop member 74A is formed just rearward of the intermediate wall 70A. The stop member 74A has a width which is less than the depth of the semi-cylindrical cavity 64A such that when the housing halves 30A, 30B are assembled, there is a space between the stop member 74A and a corresponding stop member in the opposite housing half.

At the junction between the main body portion 31A and the enlarged rear portion 40A of the right inner housing half 30A is a rear wall 76A having a semi-cylindrical opening 78A therethrough. When the inner housing halves are assembled, the rear wall 76A mates with a corresponding rear wall in the opposite housing half to form a wall having a cylindrical bore therethrough.

Within the enlarged rear portion 40A of the right housing half 30A, upper and lower walls 80A, 82A, each in the shape of a partial annulus, are formed.

The inner housing half 30A further comprises a plurality of locating pins 84 and locating holes 86 for mating with corresponding holes and pins in the opposite inner housing half 30B. A pin and a hole are located in each of the walls 66A, 70A, and 76A.

A groove 90A is formed in the upper wall of the inner housing half 30A extending between the front wall 66A and the intermediate wall 70A. Another groove 92A is formed in the lower wall of the inner housing half 30 A extending between the intermediate wall 70A and the back wall 76A. When the housing halves 30A, 30B are assembled, opposing walls of the top cannula hub guide channel 58A and of the bottom stylet hub guide channel 60A are grooved.

A semi-cylindrical recess 94A is formed in the nose portion 34A of the right housing half 30A. A semi-cylindrical recess 96A is formed in the lower portion of the intermediate wall 70A of the right housing half 30A. When the inner housing halves 30A, 30B are assembled, the semi-cylindrical channel 94A mates with a corresponding semi-cylindrical channel in the opposite inner housing half 30B to form a cylindrical bore 94 within the nose portion 34, and the semi-cylindrical recess 96A in the intermediate wall 70A mates with a corresponding semi-cylindrical recess in the opposite inner housing half 30B to form a cylindrical bore in coaxial alignment with the cylindrical bore 94.

Referring now to FIGS. 4A and 4B, a first needle hub, or cannula hub, 100 has a hollow first needle or cannula 102 extending forward therefrom. The cannula 102 is of conventional design and is formed of stainless steel or other suitable material. The cannula 102 has a sharpened forward end 103 which serves as a cutting edge. The cannula hub 100 is molded from acetal or other suitable material and includes an upright 104. An upper trailing arm 106 extends rearward from the upright at a location spaced downward from the upper end of the upright. The portion of the upright 104 which extends above the upper trailing arm 106 comprises a post 108. Guide ribs 110 extend laterally along the length of the upper trailing arm 106. A lower trailing arm 112 extends rearward from the lower end of the upright 104. The rear end of the cannula 102 extends through the lower trailing arm 112 of the cannula hub 100 and is securely anchored therewithin.

A disk-shaped member 116 is mounted to the rear edge of the upright 104 of the cannula hub 100, between the upper and lower trailing arms 106, 112. A pair of locking tangs 118 projects rearward from the disk-shaped member 116. Each of the locking tangs 118 comprises a cantilevered arm 120 which terminates at its rearward end in a flange 122. The trailing edge 124 of each of the flanges 122 is angled.

Referring now to FIGS. 5A and 5B, a second needle hub, or stylet hub, 130 has a second needle, or stylet, 131 extending forward therefrom. The stylet 131 is of conventional design and is formed of stainless steel or other suitable material. The stylet 131 is dimensioned to slide telescopically within the hollow cannula 102. The stylet 131 has a sharpened forward tip 132 and a tissue sample receiving recess 133 formed just aft of the forward tip.

The stylet hub 130 is molded from acetal or other suitable material and includes an upright 134. A V-shaped notch 135 is formed in the front face of the upright 134. A lower trailing arm 136 extends rearward from the upright 134 at a location spaced upward from the lower end of the upright. The rear end of the stylet 131 is securely anchored within the lower trailing arm 136. The portion of the upright 134 which extends below the lower trailing arm 136 comprises a post 138. Guide ribs 140 extend laterally along the length of the lower trailing arm 136. An upper trailing arm 142 extends rearward from the upper end of the upright 134.

A disk-shaped member 146 is mounted to the rear edge of the upright 134 between the lower and upper trailing arms 136, 142. A pair of locking tangs 148 projects rearward from the disk-shaped member 146. Each of the locking tangs 148 comprises a cantilevered arm 150 which terminates at its rearward end in a flange 152. The trailing edge 154 of each of the flanges 152 is angled.

The stylet hub 130 has a pair of stylet bumpers 156 mounted one on either side of the the disk-shaped member 146. In the disclosed embodiment the bumpers 156 are dumbbell-shaped, with enlarged head portions connected by a reduced neck portion. Slots are formed in the disk-shaped member 146 of the stylet hub dimensioned to receive the reduced neck portion of the bumper 156, with the inner faces of the enlarged head portions bearing against the disk-shaped member 146. In the disclosed embodiment the bumpers are comprised of silicone having a hardness of 65–75 on the Shore A scale.

FIGS. 6A–6C illustrate a lower cocking slide 160. The lower cocking slide 160 comprises a nose portion 162 having a front face 164 adapted to receive a finger of an operator. A neck 166 extends downward from the rear edge of the nose portion 162. A bridge 168 extends rearward from the lower end of the neck 166. The upper surface 169 of the bridge 168 is concave and generally conforms to the curvature of the cylindrical main body portion 31 of the inner housing 30. An elongated trough 170 is formed in the upper surface 169 of the bridge 168 of the stylet cocking slide 160 along its longitudinal axis. A rectangular opening 172 is formed in the bridge 168 adjacent its rearward end. A pair of upward extending side walls 174 are formed at the rear end of the bridge 168 along the lateral edges thereof. A pair of opposed flanges 176 extend inward from the upstanding side walls 174.

FIGS. 7A–7C illustrate an upper cocking slide 180. The upper cocking slide 180 has a front face 182 adapted to receive a finger of an operator. The lower surface of the upper cocking slide 180 is concave and is configured to conform generally to the upper surface of the cylindrical main body portion 31 of the inner housing 30. A rectangular opening 184 is formed in the upper surface of the upper cocking slide 180. A pair of opposed, inward extending flanges 186 are formed on the concave lower surface of the upper cocking slide 180.

FIGS. 8A–8C illustrate a retainer 190. The retainer 190 has a generally rounded nose 192 having a circular hole 194 formed therethrough. An upper wall 196 of the retainer 190 has a pair of rectangular openings 198 formed therein. The back edge 200 of the retainer 190 is angled to correspond to the angled front end 15 of the outer housing 14.

With particular reference to FIG. 8C, the bottom wall 202 of the retainer 190 has the same radius of curvature as the outer housing 14. An arcuate inner wall 204 forms an annular space between it and the bottom outer wall 202 of the retainer 190. A plurality of fingers 206 extend from the inner wall 204 toward, but terminating short of, the outer wall 202.

Figure 9A:
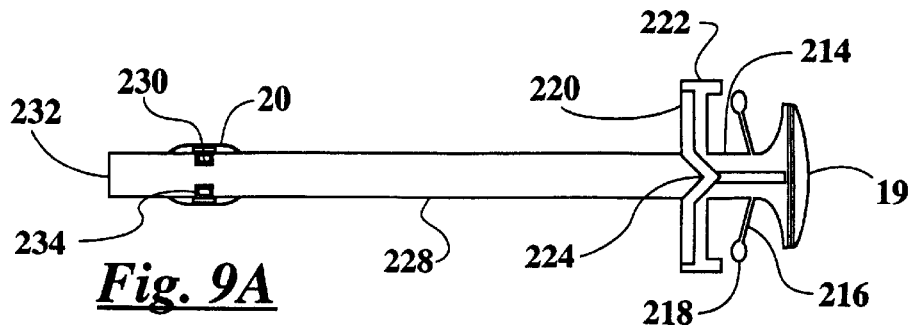
FIG. 9A is a side view of a trigger assembly of the biopsy instrument of FIG. 1.
Figure 9B:
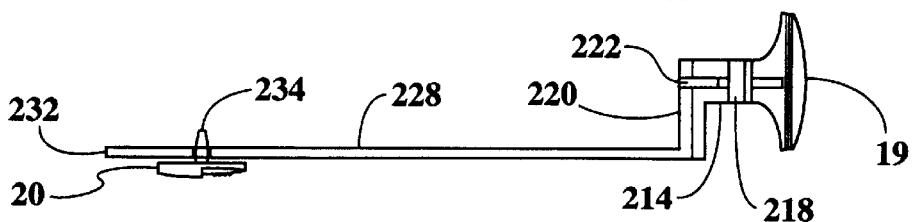
FIG. 9B is a top view of the trigger assembly of FIG. 9A.

Referring now to FIGS. 9A and 9B, a trigger assembly 210 is illustrated. The trigger assembly 210 includes the rear trigger button 19 that is located at the rearward end of the trigger assembly 210. A stem 214 extends forward from the rear trigger button 19. A pair of cantilevered arms 216 having enlarged end portions 218 extends outward and forward from the stem 214. A cross member 220 having trailing end portions 222 is connected to the forward end of the stem 214. A V-shaped notch 224 is formed in the front face of the cross member 220.

A link arm 228 extends laterally outward and forward from the cross member 220. The link arm 228 has a pair of opposed notches 230 adjacent its forward end 232. The side trigger button 20 has a pair of spaced-apart prongs 234 projecting from its back face. The prongs 234 engage the notches 230 in the link arm 228 of the trigger assembly 210 to couple the side trigger button 20 to the trigger assembly 210.

Assembly of the biopsy instrument 10 will now be explained with reference to FIGS. 10–14. Referring first to FIG. 10, the cannula hub 100, stylet hub 130, trigger assembly 210, and first and second coil springs 240, 242 are positioned within one of the interior housing halves (right housing half 30A is shown in FIG. 10). The coil springs 240, 242 are comprised of stainless steel and have a spring rating of nominally 4.53 pounds per inch. Before positioning the needle hubs 100, 130 within the inner housing half 30A, the forward tip of the stylet 131 is inserted through the back end of the cannula and advanced until the stylet tip protrudes slightly from the forward end 103 of the cannula 102. Prior to the stylet hub 130 being positioned onto the housing half 30A, the first coil spring 240 is positioned over the locking tangs 148 and between the lower and upper trailing arms 136, 142 of the stylet hub 130. As the stylet hub 130 is positioned onto the inner housing half 30A, the rear of the coil spring 240 is positioned against the front face of the back wall portion 76A. Similarly, prior to positioning the cannula needle hub 100 onto the inner housing half, the second coil spring 242 is positioned over the locking tangs 118 and between the upper and lower trailing arms 106, 112 of the cannula hub. As the cannula hub 100 is assembled onto the inner housing half 30A, the back end of the coil spring 242 is positioned against the forward face of the intermediate wall portion 70A.

When the cannula hub 100 is positioned onto the inner housing half 30A, the guide ribs 110 on the upper trailing arm 106 of the cannula hub are received within the groove 90 in the upper wall of the inner housing half. Similarly, when the stylet hub 130 is positioned onto the inner housing half, the guide ribs 140 on the lower trailing arm 136 of the stylet hub are received within the groove 92 in the lower wall of the inner housing half.

The trigger assembly 210, minus the side-mounted trigger button 20, is mounted within the enlarged back portion 40A of the inner housing half 30A. The enlarged end portions 218 of the cantilevered arms 216 of the trigger assembly 210 are positioned against the back surface of the walls 80A, 82A, while the trailing end portions 222 of the cross member 220 bear against the front face of the walls 80A, 82A. When thus mounted, the cantilevered arms 216 will deflect when the rear trigger button 19 is depressed and will return the trigger assembly 210 to its normal position when pressure is released.

In. FIG. 11, the two inner housing halves 30A, 30B have been assembled, capturing the needle hubs 100, 130, the springs 240, 242, and trigger assembly 210 within the inner housing 30. The two inner housing halves 30A, 30B are mated by inserting the pins 84 from one housing half into the corresponding holes 86 in the other housing half. The upper and lower trailing arms 106, 112 of the cannula hub 100 ride within the cannula hub guide channels 58 formed in the upper and lower surfaces of the inner housing 30, and the post 108 of the cannula hub 100 projects upward through the upper cannula hub guide channel 58. Similarly, the lower and upper trailing arms 136, 142 of the stylet hub 130 ride within the stylet hub guide channels 60 formed in the upper and lower surfaces of the inner housing 30, and the post 138 of the stylet hub 130 projects downward through the bottom stylet hub guide channel 60. The trailing end portions 222 of the cross member 220 of the trigger assembly 210 ride within the trigger assembly retention slots 62 in the upper and lower walls of the enlarged cylindrical rear portion 40 of the inner housing 30.

As can also be seen in FIG. 11, the link arm 228 of the trigger assembly 210 passes through the rectangular opening 42 in the rear portion 40 of the left inner housing half 30B and then extends between the guide tabs 52 on the side of the inner housing 30. The forward portion of the link arm 228 rests on the two raised tabs 50 on the side of the inner housing 30, and the notches 230 in the link arm 228 overlie the rectangular opening 48 in the side of the inner housing 30.

FIG. 12 shows the assembly of the lower and upper cocking slides 160, 180 onto the inner housing 30. The inwardly extending flanges 176 of the lower cocking slide engage the longitudinal grooves 46 on the lower portion of the inner housing 30. The post 138 of the stylet hub 130 which extends downward through the lower stylet hub guide channel 60 in the inner housing 30 is captured within the rectangular opening 172 in the lower slide 160, thereby coupling the stylet hub to the lower cocking slide.

The forward portion of the upper cocking slide 180 overlies the forward portion of the lower cocking slide 160, the front wall 182 of the upper cocking slide being aligned with the front wall 164 of the lower cocking slide 160. The inwardly extending flanges 186 of the upper cocking slide 180 engage the grooves 44 on the outer surface of the inner housing 30. The upstanding post 108 of the cannula hub 100 which projects through the upper cannula hub guide channel 58 in the inner housing 30 is captured within the rectangular opening 184 of the upper slide 180, thereby coupling the cannula hub 100 to the upper slide 180.

In FIG. 13 the assembly is inserted into the outer housing 14. The forward portions of the lower and upper cocking slides 160, 180 extend from the opening at the forward end 15 of the outer housing 14. The rectangular opening 26 in the outer housing 14 is in register with the rectangular opening 48 in the inner housing 30, and the notches 230 and the link arm 228 of the trigger assembly 210 are visible through the opening 26. The locating pins 43 on the rear portion 40 of the inner housing 30 snap into the corresponding locating holes 27 in the outer housing 14 to retain the inner housing within the outer housing.

In FIG. 14 the retainer 190 has been assembled onto the outer housing 14. The tongue 22 of the outer housing 14 is received between the lower ends of the tabs 206 and the bottom wall 202 of the retainer 190. The needle assembly 11 is received through the round hole 194 in the nose of the retainer 190. The angled upsets 36 on the nose 34 of the inner housing 30 snap into the rectangular openings 198 in the upper wall 196 of the retainer 190, preventing the retainer from being dislodged. Further advancement of the retainer is prevented by the back edge of the upper wall 196 of the retainer 190 confronting the raised stop members 38 on the inner housing 30.

As is also illustrated in FIG. 14, the side mounted trigger button 20 is installed, the prongs 234 of the trigger slide 20 being inserted through the rectangular opening 26 of the outer housing 14 and engaging the notches 230 in the link arm 228 of the trigger assembly 210.

Figure 15:
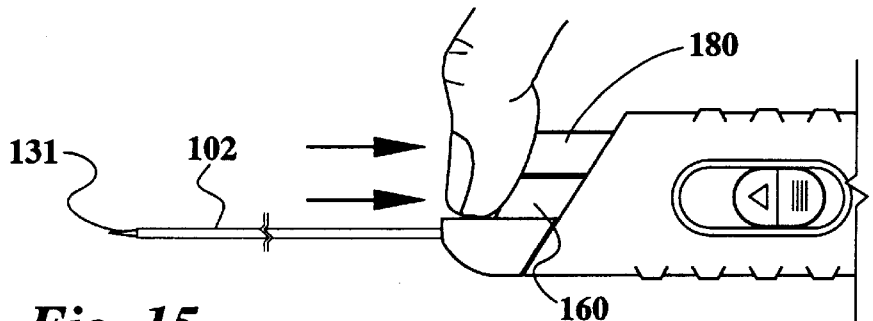
FIG. 15 is a partial side view of the biopsy instrument of FIG. 1 showing the cannula and stylet cocking slides being cocked simultaneously.
Figure 16A:
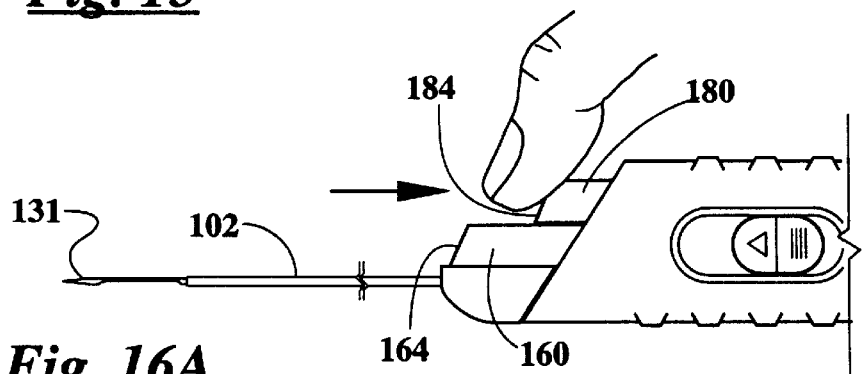
FIGS. 16A and 16B are partial side views of the biopsy instrument of FIG. 1 showing the stylet and cannula cocking slides being cocked sequentially, with FIG. 16A showing the cannula slide being cocked and FIG. 16 showing the stylet slide being cocked.
Figure 16B:
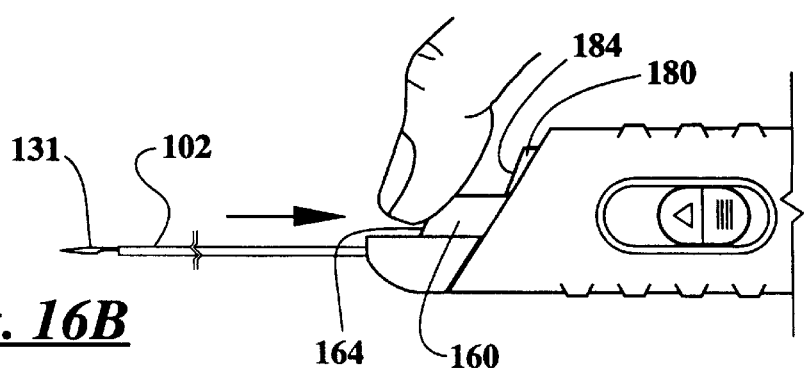

Before operating the biopsy instrument 10, the physician must first cock the device. At the physician's option, the cannula 102 and stylet 131 may be cocked simultaneously by placing a finger across the bearing surfaces of both the lower and upper slides 160, 180 and biasing both slides rearward simultaneously, as illustrated in FIG. 15. Or, the cannula 102 and stylet 131 can be cocked sequentially, by the physician first placing a finger only on the front wall 182 of the upper cocking slide 180 and biasing it rearward, as shown in FIG. 16A, followed by the physician placing a finger on the front wall 164 of the lower cocking slide 160 and biasing the stylet rearward, as shown in FIG. 16B.

With the device 10 thus cocked according to either of these two methods, the needle assembly 11 is introduced into the patient and advanced until the sharpened tip 132 of the stylet 131 lies adjacent to the target tissue to be sampled. Positioning of the needle assembly 11 with respect to the target tissue can be accomplished either by means of suitable visualization technology, such as ultrasound and an associated needle guide, or manually by the physician's finger in conjunction with palpation.

Figure 17:
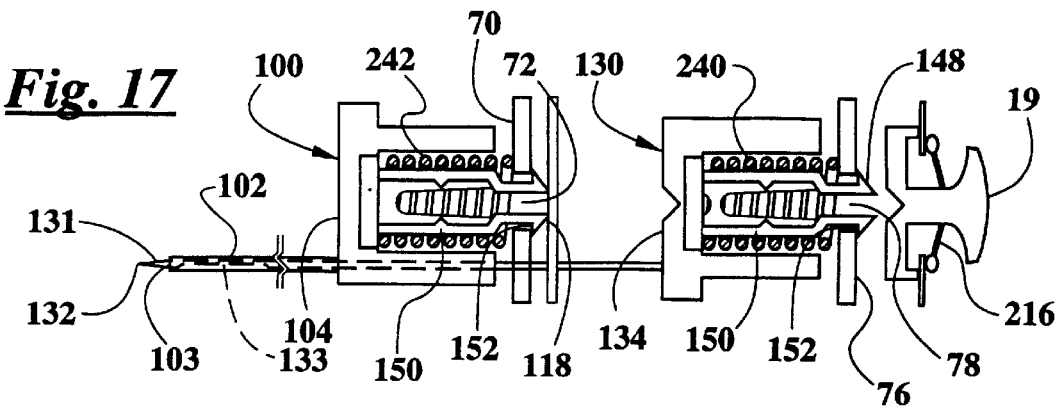
FIGS. 17–20 illustrate a firing sequence of a biopsy instrument according to the present invention, where

Operation of the device will now be explained with reference to FIGS. 17–20. FIG. 17 shows the stylet 131 and cannula 102 in their respective cocked positions. The locking tangs 148 of the stylet hub 130 extend through the circular opening 78 in the rear wall 76, the flanges 152 at the ends of the cantilevered arms 150 engaging the back face of the rear wall 76 to retain the stylet hub in the locked position. With the stylet hub thus cocked, the first coil spring 240 is compressed between the back face of the upright 134 of the stylet hub 130 and the front face of the rear wall 76. The locking tangs 148 thus comprise a first latch means for releasably holding the first coil spring 240 in an energized mode. Similarly, the locking tangs 118 of the cannula hub 100 extend through the circular opening 72 in the intermediate wall 70, with the flanges 152 of the locking tangs engaging the back face of the intermediate wall 70. With the cannula thus cocked, the second coil spring 242 is compressed between the back face of the upright 104 of the cannula hub 100 and the front face of the intermediate wall 70. The locking tangs 118 thus comprise a second latch means for releasably holding the second coil spring 242 in an energized mode. The trigger button 19 is maintained in its raised position by the s cantilevered arms 216 of the trigger assembly 210.

With the stylet and cannula both cocked, the sharpened tip 132 of the stylet 131 protrudes slightly from the front end 103 of the cannula 102, with the tissue receiving recess 133 of the stylet being retracted within the forward end of the cannula.

Figure 18:
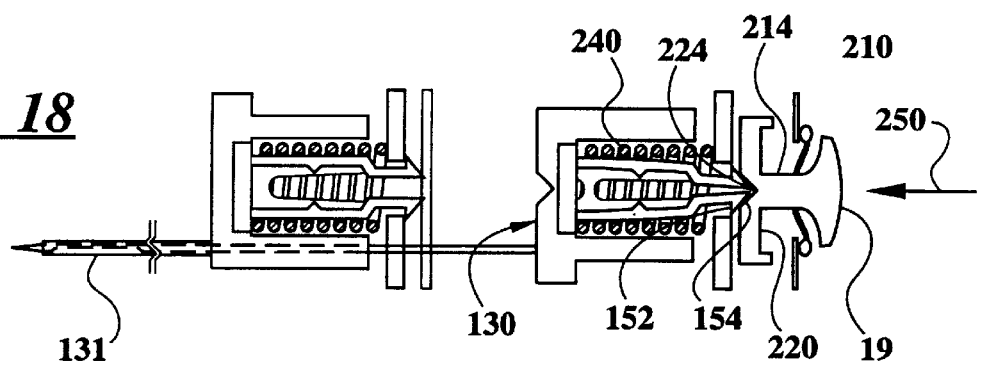

Referring now to FIG. 18, once the forward end of the needle assembly has been properly positioned within the patient, the physician actuates the instrument 10 by depressing either the rear trigger button 19 or the side trigger button 20. Depression of the rear trigger button 19 in the direction indicated by the arrow 250 exerts a forward force against the cross member 220 of the cocking assembly 210 through the stem 214. Advancing the side trigger button 20 (not shown in FIG. 18) exerts a forward force against the cross member 220 through the link arm 228. As the cross member 220 moves forward, the V-shaped notch 224 in the front face of the cross member confronts the trailing edges 154 of the locking tangs 150 of the stylet hub 130, collapsing the tangs and disengaging the flanges 152 from the rear wall 76. The stylet hub 130 and associated stylet 131 are then driven forward by the first coil spring 240.

Figure 19:
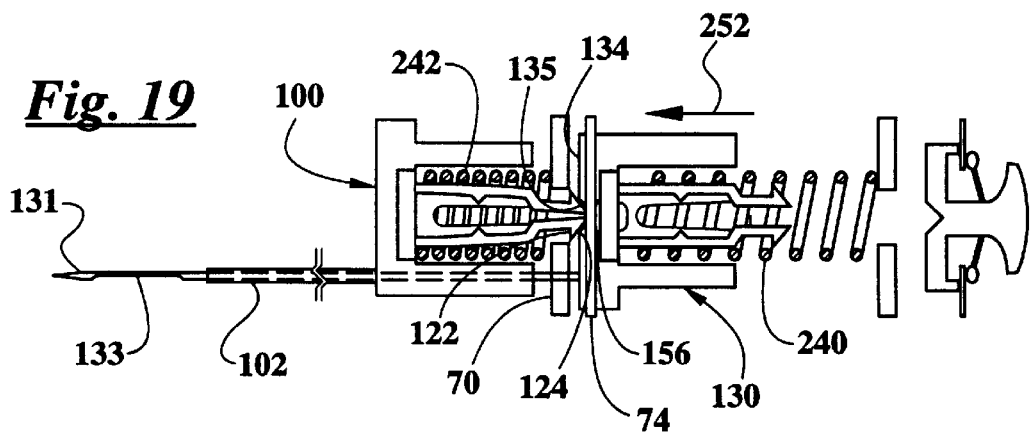

Referring now to FIG. 19, the stylet hub 130 has been driven forward in the direction indicated by the arrow 252. The tissue receiving recess 133 adjacent the forward end of the stylet 131 now extends from the cannula 102 such that tissue is permitted to prolapse into the recess. Near the forward limit of the range of movement of the stylet hub 130, the stylet bumpers 156 strike the stop 74. The forward momentum of the stylet hub 130 causes the stylet bumpers 156 to deform, such that the stylet hub continues to advance approximately another 1 millimeter. The V-shaped notch 135 in the front face of the upright 134 of the stylet hub 130 confronts the angled trailing edges 124 of the locking tangs 118 of the cannula hub 100, collapsing the locking tangs and disengaging the flanges 122 from the intermediate wall 70. The cannula hub 100 is now free to be driven forward by the second coil spring 242.

Figure 20:
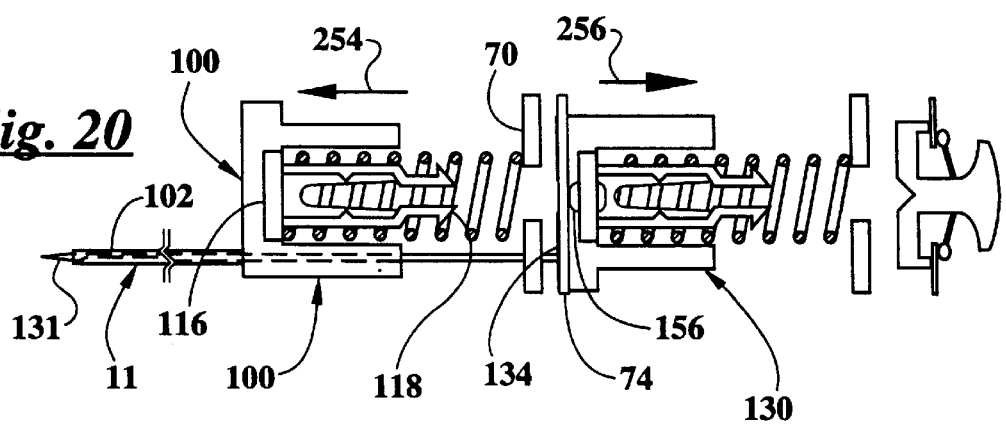

In FIG. 20, the cannula hub 100 has been driven forward in the direction indicated by the arrow 254 and has reached the forward extent of its travel. The lateral edges of the front face of the disk-shaped member 116 of the cannula hub strike the stops 68 on the inner housing, preventing further forward movement of the cannula hub. The cannula 102 has advanced over the stylet 131 and sheared off the tissue which has prolapsed into the tissue receiving recess 133 of the stylet, capturing it within the forward end of the cannula. The physician then withdraws the needle assembly 11 from the patient.

As is also shown in FIG. 20, once the forward momentum of the stylet hub 130 has been expended, the resilient stylet bumpers 156 exert a rearward force against the stylet hub in the direction indicated by the arrow 256 as they return to their normal state, displacing the stylet hub slightly rearward. The upright 134 of the stylet hub 130 is thus spaced sufficiently from the intermediate wall 70 of the inner housing 30 that when the cannula hub 100 is again cocked, the V-shaped notch in the stylet hub 130 will not colprolapse the locking tangs 118 of the cannula hub. Without the rearward displacement effected by the stylet bumpers 156, it would be impossible for the locking tangs 118 of the cannula hub 100 to engage the intermediate wall 70 of the inner housing without the stylet hub 130 being cocked first, because the V-shaped notch 135 in the front face of the stylet hub 130 would prevent the locking tangs 118 of the cannula hub 100 from moving outward to engage the intermediate wall 70.

From the foregoing description, it will be apparent that the location of the stops 68, 74 within the inner housing 30 relative to the location of the needle hubs 100, 130 in their respective cocked positions determines the extent of travel, or "throw," of the needles 102, 131. The throw of the needles can thus be controlled by relocating the stops 68, 74, by moving the walls 66, 70, by changing the length of the locking tangs 118, 148, or by various combinations of these factors.

To recover the tissue specimen, the physician places a finger on the front wall 182 of the upper cocking slide 180, but not the lower cocking slide 160, as shown in FIG. 16A, and retracts the upper cocking slide rearward. This action retracts the cannula 102, leaving the stylet 131 in its extended position. As the cannula 102 retracts, the tissue receiving recess 133 of the stylet 131 with captured tissue specimen is uncovered, providing access to the tissue specimen.

Once the tissue specimen has been recovered, the physician can ready the instrument 10 for a second use on the same patient by cocking the lower cocking slide 160, thereby bringing the stylet 131 to its energized position.

As can be seen, the biopsy instrument 10 provides several advantages over prior art automated biopsy devices. The device 10 permits single handed cocking. It further permits the needles 102, 131 to be cocked either simultaneously or sequentially, at the option of the physician. Thus, when it is necessary to retrieve a tissue specimen from the needle assembly 11, the physician can cock the cannula 102 without cocking the stylet 131, thereby exposing the tissue receiving recess 133 without having to dismount the needle assembly 11 from the driving unit 12. However, where recovery of a tissue specimen from the needle assembly 11 is not involved, the physician can cock both the cannula 102 and the stylet 131 simultaneously, as hereinabove described.

Another advantage provided by the biopsy instrument 10 of the present invention is that because of the arrangement of the cocking slides 160, 180, the sequence in which the slides should be cocked is intuitive to the physician. Specifically, the finger-contacting portion 164 of the lower cocking slide 160 when the slide in its cocked position is located rearward of a location defined by the finger contacting portion 182 of the upper cocking slide 180 when the upper cocking slide is in its uncocked position. Stated differently, if the upper cocking slide 180 is in its uncocked position, the physician cannot move the lower cocking slide 160 to its cocked position without his finger first contacting the finger receiving portion 182 of the upper cocking slide. This relative relationship between the upper and lower cocking slides ensures that the physician will either cock the upper slide 180 first or will cock the slides simultaneously.

Still another advantage provided by the biopsy instrument 10 of the present invention is that the physician can easily tell, either visually or tactilely, whether the device is fully cocked, half-cocked, or uncocked. When the instrument is uncocked, both the lower and upper slides 160, 180 extend from the front 15 of the outer housing 14. When the instrument is cocked, both the lower and upper slides 160, 180 are retracted within the forward end of the outer housing 14. The physician can confirm either visually or by feeling the forward end of the device 10 whether the slides 160, 180 are extended from the front 15 of the outer housing 14 or retracted into the front end of the outer housing, or whether one slide is extended and the other retracted.

Yet another advantage provided by the biopsy instrument 10 of the present invention is that the physician can fire the device from either of two trigger locations. Depending upon the orientation of the biopsy instrument 10 during the tissue retrieval process, depending upon the nature of the procedure being performed, and depending upon the personal preference of the physician, the device can be fired either by depressing the rear trigger button 19 at the rear of the device, or by advancing the side trigger button 20 adjacent the front of the device.

As previously stated, the bumpers 156 of the disclosed embodiment are comprised of silicone having a hardness on the Shore A scale of 65–75. Another important characteristic of the silicone of which the bumpers are comprised is that it have a relatively high resistance to compression set, that is, that it be sufficiently resilient to return substantially to its normal shape. It is the resilience of the bumper material which provides the bumpers 156 with the capacity to return substantially to their normal shapes which provides the force to back the stylet hub 130 away from the intermediate wall 70.

While the stylet bumpers 156 of the disclosed embodiment are comprised of silicone having a hardness of 65–75 on the Shore "A" scale, it will be appreciated that this material was selected based on the characteristics of the coil springs 240, 242. Changing the characteristics of the springs will require changing the properties of the stylet bumpers. For example, a stronger spring will require that the bumpers 156 be comprised of a more resilient material to exert sufficient rearward force to overcome the force of the springs. On the other hand, since a stronger spring will impart greater momentum to the stylet hub 130, the stylet bumpers can be comprised of a harder material that is more difficult to deform. Conversely, a weaker spring will not be able to deform the stylet bumpers 156 sufficiently to permit the stylet hub 130 to colprolapse the locking tangs 118 of the cannula hub, so a softer bumper material will be required. However, since less rearward force need be exerted by the stylet bumpers 156 to overcome the force of a weaker spring, the bumper material would not need to be as resilient.

Finally, it will be understood that the preferred embodiment has been disclosed by way of example, and that other modifications may occur to those skilled in the art without departing from the scope and spirit of the appended claims.

What is claimed is:

1. A tissue sampling device comprising:

an inner housing having front and rear inner housing ends and a longitudinal axis extending between said front and rear inner housing ends, said inner housing further having an exterior surface and having longitudinally extending slots formed therein, and said front inner housing end having an opening therethrough;

first and second needle hubs mounted within said inner housing for movement along said longitudinal axis of said inner housing;

a hollow first needle having one end coupled to said first needle hub, said hollow first needle extending along said longitudinal axis of said housing through said opening in said front inner housing end;

a second needle slidably disposed within said hollow first needle, said second needle having a tip at one end and an opposite end coupled to said second needle hub, and said second needle having a tissue sample receiving recess adjacent said tip;

a first spring operatively associated with said second needle hub and said inner housing, said first spring being capable of being placed in an energized mode to store energy, and said first spring being releasable from said energized mode to propel said second needle hub along said axis toward said opening such that said tissue sample receiving recess of said second needle is extended from said hollow first needle, whereby a tissue sample can be captured within said recess;

a second spring operatively associated with said first needle hub and said inner housing, said second spring being capable of being placed in an energized mode to store energy, and said second spring being releasable from said energized mode to propel said first needle hub along said axis toward said opening such that said tissue sample receiving recess of said second needle is enclosed by said hollow first needle;

a first latch means selectively releasable from outside said inner housing for releasably holding said first spring in said energized mode;

a second latch means for releasably holding said second spring in said energized mode, said second latch means being releasable in response to and subsequent to release of said first latch means;

a first slide mounted to said exterior surface of said inner housing, said first slide being movable between a first position and a second position, said first slide having a finger receiving portion, and said first slide being coupled to said first needle hub through said longitudinal slots in said inner housing such that said first needle hub can be retracted by exerting a rearward force against said finger receiving portion of said first slide to move said first slide from its first position to its second position to place said second spring in said energized mode; and a second slide mounted to said exterior surface of said inner housing and movable between a first position and a second position, said second slide having a finger receiving portion, and said second slide being coupled to said second needle hub through said longitudinal slots in said inner housing such that said second needle hub can be retracted by exerting a rearward force against said finger receiving portion of said second slide to move said second slide from its first position to its second position to place said first spring in said energized mode; and an outer housing surrounding said inner housing and a major portion of said first and second slides, said finger receiving portions of said first and second slides being accessible through said outer housing.

2. The tissue sampling device of claim 1, further comprising retaining means for retaining said inner and outer housings in fixed relation to one another.

3. The tissue sampling device of claim 1, wherein said outer housing comprises an opening at a forward end thereof, and wherein said first and second slides are configured such that said finger receiving portions of said first and second slides are accessible through said opening at said forward end of said outer housing.

4. The tissue sampling device of claim 1, further comprising a trigger mounted to said inner housing and selectively operable to release said first latch means, said trigger being actuatable from without said outer housing.

5. The tissue sampling device of claim 4, wherein said trigger comprises a rear trigger button at said rear inner housing end, wherein said outer housing has an opening at a rear end thereof, and wherein said rear trigger button is accessible through said opening at said rear end of said outer housing.

6. The tissue sampling device of claim 4, wherein said trigger comprises a longitudinal linkage extending between said inner and outer housings to a location spaced forward from said rear inner housing end, said tissue sampling device further comprising a forward trigger button mounted to said outer housing and coupled to said longitudinal trigger linkage through an aperture in said outer housing.

7. The tissue sampling device of claim 5, wherein said trigger further comprises a longitudinal linkage extending between said inner and outer housings to a location spaced forward from said rear inner housing end, said tissue sampling device further comprising a forward trigger button mounted to said outer housing and coupled to said longitudinal trigger linkage through an aperture in said outer housing, whereby said trigger can be actuated by manipulating either said forward trigger button or said rear trigger button.

* * * * *